(12) United States Patent
Pougnas

(10) Patent No.: US 11,304,905 B2
(45) Date of Patent: Apr. 19, 2022

(54) SOLID COMPOSITION FOR QUICK INGESTION WITH FACILITATED SWALLOWING, IN THE FORM OF SOLID, NON-AGGLOMERATED PARTICLES, COMPRISING TWO DIFFERENT TYPES OF PARTICLES

(71) Applicant: Unither Pharmaceuticals, Amiens (FR)

(72) Inventor: Jean-Luc Pougnas, Libourne (FR)

(73) Assignee: Unither Pharmaceuticals, Amiens (FR)

( * ) Notice: Subject to any disclaimer, the term of this patent is extended or adjusted under 35 U.S.C. 154(b) by 0 days.

(21) Appl. No.: 16/330,288

(22) PCT Filed: Sep. 15, 2017

(86) PCT No.: PCT/FR2017/052476
§ 371 (c)(1),
(2) Date: May 28, 2019

(87) PCT Pub. No.: WO2018/051039
PCT Pub. Date: Mar. 22, 2018

(65) Prior Publication Data
US 2019/0201343 A1 Jul. 4, 2019

(30) Foreign Application Priority Data

Sep. 15, 2016 (FR) ..................................... 1658666

(51) Int. Cl.
| | |
|---|---|
| *A61K 9/14* | (2006.01) |
| *A61K 9/16* | (2006.01) |
| *A61K 9/00* | (2006.01) |
| *A61K 31/167* | (2006.01) |
| *A61K 31/192* | (2006.01) |
| *A61K 31/606* | (2006.01) |
| *A61K 36/05* | (2006.01) |
| *A61K 36/28* | (2006.01) |
| *A61K 36/324* | (2006.01) |
| *A61K 36/81* | (2006.01) |
| *A61K 36/9066* | (2006.01) |
| *A61K 36/9068* | (2006.01) |

(52) U.S. Cl.
CPC ............ *A61K 9/1623* (2013.01); *A61K 9/009* (2013.01); *A61K 9/0056* (2013.01); *A61K 9/145* (2013.01); *A61K 31/167* (2013.01); *A61K 31/192* (2013.01); *A61K 31/606* (2013.01); *A61K 36/05* (2013.01); *A61K 36/28* (2013.01); *A61K 36/324* (2013.01); *A61K 36/81* (2013.01); *A61K 36/9066* (2013.01); *A61K 36/9068* (2013.01)

(58) Field of Classification Search
CPC .......... A61K 9/14; A61K 9/141; A61K 9/143; A61K 9/145; A61K 9/16; A61K 9/1605; A61K 9/1623; A61K 9/148
See application file for complete search history.

(56) References Cited

U.S. PATENT DOCUMENTS

| | | | | |
|---|---|---|---|---|
| 5,674,533 | A * | 10/1997 | Santus | ................... A61P 11/14 424/493 |
| 7,067,149 | B1 | 6/2006 | Chauveau et al. | |
| 2001/0009678 | A1 | 7/2001 | Toshihiro et al. | |
| 2002/0068088 | A1 | 6/2002 | Gruber | |
| 2007/0092553 | A1 * | 4/2007 | Tengler | ................ A61K 9/0056 424/440 |
| 2012/0220625 | A1 | 8/2012 | Rowe et al. | |
| 2013/0052278 | A1 | 2/2013 | Rich et al. | |

FOREIGN PATENT DOCUMENTS

| | | |
|---|---|---|
| EP | 1 802 285 B1 | 7/2007 |
| EP | 2216048 | 8/2010 |
| JP | 2000119173 A | 4/2000 |
| JP | 2001064159 A | 3/2001 |
| JP | 2012246252 A | 12/2012 |
| WO | 2008/037555 | 4/2008 |

OTHER PUBLICATIONS

Simone Schiermeier, et al., (2002), European Journal of Pharmaceutical Sciences, "Fast dispersible ibuprofen tablets", vol. 15, pp. 295-305.

Gerad K. Bolhuis, et al., (2009), Drug Development and Industrial Pharmacy, "Polyols as filler-binders for disintegrating tablets prepared by direct compaction", vol. 35, No. 6, pp. 671-677.

* cited by examiner

*Primary Examiner* — Micah Paul Young
(74) *Attorney, Agent, or Firm* — McDonnell Boehnen Hulbert & Berghoff LLP

(57) ABSTRACT

A solid composition with rapid ingestion and facilitated swallowing, in the form of non-agglomerated solid particles, said composition comprising the following two different types of particle:

Pa particles, with very low solubility in saliva and comprising at least one active ingredient, and Ps particles, rapidly soluble in saliva, characterised by an apparent density equal to or greater than approximately 0.6 g.cm$^{-3}$, advantageously equal to or greater than approximately 0.7 g.cm$^{-3}$, and preferably between 0.7 and 1.5 g.cm$^{-3}$ inclusive.

18 Claims, No Drawings

SOLID COMPOSITION FOR QUICK INGESTION WITH FACILITATED SWALLOWING, IN THE FORM OF SOLID, NON-AGGLOMERATED PARTICLES, COMPRISING TWO DIFFERENT TYPES OF PARTICLES

CROSS REFERENCE TO RELATED APPLICATIONS

This application is a US national phase of International Application No. PCT/FR2017/052476, filed on Sep. 15, 2017, which claims benefit from FR Patent Application No. 1658666, filed on Sep. 15, 2016, the entire contents of each of which are incorporated herein by reference.

TECHNICAL FIELD

The present invention concerns the field of solid oral compositions, for pharmaceutical or nutritional purposes, suitable to be administered to a human or animal individual. More particularly, the invention relates to a solid galenic form with rapid ingestion and facilitated swallowing.

STATE OF THE ART

Solid oral compositions (such as in particular medicines or food supplements/nutritional compositions) generally come in the form of capsules or tablets.

One of the main problems posed by oral administration of solid forms such as tablets or capsules is swallowing. Indeed, approximately 35% of people in the median age group of the population suffer from dysphagia problems and struggle to swallow tablets or capsules. This percentage is significantly greater among young children and the elderly, not to mention mentally impaired or medically uncooperative persons. Such difficulties are a considerable factor in the poor compliance—or non-compliance—with treatments (in particular for long-term treatments).

In response to this problem, pharmaceutical compositions have been developed with the aim of obtaining solid galenic forms, which when administered orally to patients with difficulties in swallowing, such as children, the elderly, medically uncooperative individuals with mental impairments, etc., are capable of breaking down (i.e. fragmenting or disintegrating) rapidly, without the need for exogenous water intake, thereby facilitating the swallowing process.

Various solid galenic forms intended to break down rapidly—or relatively rapidly—in the mouth have been used. These are primarily oral lyophilisates, effervescent oral tablets, or more recently, chewable tablets or tablets with a high breakdown agents content.

Oral lyophilisates (or freeze drying tablets) represent the most commonly used rapid-breakdown compositions, in particular due to the fact that they ensure very rapid disintegration after oral administration, because of their high hygroscopicity and high porosity. Nonetheless, these lyophilisates present certain drawbacks, such as:
  i) high fragility when handled, because of their high friability,
  ii) high sensitivity to atmospheric moisture, and
  iii) complex technology and manufacturing method and, consequently, high manufacturing costs. Hence, this technology is generally selected for expensive active principles with low doses in the pharmaceutical composition.

Effervescent oral tablets are made up of a pharmaceutical composition comprising an effervescent couple, which is activated upon contact with saliva, thereby ensuring complete breakdown of the tablet. However, these effervescent tablets must necessarily be of compact size in order to ensure breakdown in the mouth taking less than 3 minutes, to limit the quantity of gas emitted and to limit the characteristic bad taste in the mouth. Another drawback of these effervescent tablets is that they are highly moisture-sensitive, which entails using a highly particular manufacturing method, typically in a controlled atmosphere.

For some years, new forms have appeared on the market, in particular in the pharmaceutical field, such as chewable (or edible) tablets, or orally disintegrating tablets. The latter have become very popular, since they present the advantage of disintegrating in the oral cavity within a few seconds, thereby avoiding the need for a swallowing effort by the patient/subject. While they have proven practical for the patient/subject, orally disintegrating tablets have generally complex compositions which, as a general rule, contain a significant number of ingredients of different kinds, including rapid-action disintegrating agents (also known as "disintegrating" agents or even "super-disintegrating" agents), which enable the tablet to break down within a few seconds in the oral cavity. U.S. Pat. No. 5,464,632 discloses, for example, tablets with a high disintegrating agents content. In particular, this patent discloses a pharmaceutical composition comprising in particular, as disintegrating agents associated with swelling agents, a high mass fraction of carboxymethyl cellulose and a cross-linked and insoluble polyvinylpyrrolidone (PVP). This composition is obtained by mixing an active ingredient, used in the form of microcrystals or microgranules, with a mixture of pre-granulated excipients. This high mass fraction of disintegrating agents in the compositions according to this document (and in particular of cross-linked and insoluble PVP) presents the drawback of generating a chalky type taste and an undesirable feeling of dryness, upon introducing these tablets incorporating them into the mouth. Similarly, patent application US 2001/0009678 discloses orally disintegrating tablets, comprising:
  a) a pharmaceutically active ingredient,
  b) one or more "sugar alcohol(s)", and
  c) a disintegrating agent, namely low-substituted hydroxypropyl cellulose comprising 7.0 to 9.9 percent by weight "hydroxypropoxyl" groups. Moreover, US 2001/0009678, in its "Working Example 5", sets out the preparation of an orally disintegrating tablet comprising not one, but two types of different disintegrating agents, namely the aforesaid low-substituted hydroxypropyl cellulose and crospovidone (also known as cross-linked polyvinylpyrrolidone).

Furthermore, it should be pointed out that these orally disintegrating tablets, in spite of all this, require a considerable time period (frequently of up to 30 seconds) to obtain the desired breakdown, which is not ideal if the patient/subject poses risks of "going wrong", as in cases of mentally impaired individuals (such as patients afflicted with Alzheimer's, schizophrenia, etc.). Furthermore, it should also be noted that an extended oral disintegration/breakdown time might promote oral absorption (or per-oral absorption) of the active ingredients present in this type of composition. This oral absorption phenomenon, is by its nature, prone to modify the bioavailability of the active ingredient(s) contained in the orally disintegrating tablet. Hence, an extended dwell time in the mouth can prove particularly disadvantageous in the sense that it is particularly prone to affect the bioequivalence of said orally disintegrating tablets. Indeed, usually, the person skilled in the art develops orally disintegrating tablets with a view to making "improved" versions of traditional tablets with the objective of improving patient comfort when taking them. In terms of pharmacokinetics, these orally disintegrating tablets must remain bio-equivalent to existing traditional tablets, namely they must possess similar properties to the latter in terms of bioavailability. Yet certain active principles may exhibit absorption in the oral mucosa, which is generally proportional to the oral dwell time. If such absorption takes place due to an extended/prolonged oral dwell time, there is a risk of significantly modifying bioavailability, and of leading to non-bioequivalence of said improved composition. This is not desirable and can prove highly detrimental, since it would then be necessary to conduct costly new clinical studies with the object of measuring the impact of the change in bioavailability with regard to efficacy and safety of using the new formulation.

In pharmaco-technical terms, a major constraint concerns the limit mass of the orally disintegrating tablets and of the active principle(s) that they contain. Indeed, these orally disintegrating tablets possess, most of the time, a mass of less than 500 mg and contain a quantity of active ingredient(s) rarely greater than 200 mg, so as to be able to break down in the oral cavity preferably in less than 30 seconds.

In purely taste terms, it is generally disadvantageous to have an extended oral dwell time, in particular if the active ingredient(s) has (have) unpleasant taste(s). That is why orally disintegrating tablets generally contain one or more compounds making it possible to mask the unpleasant taste of the active ingredients that they contain (taste-masking agent(s)), such as insoluble or low-solubility polymers. By way of example, mention may be made of patent application WO 2006/047493 (corresponding to EP-A-1802285), which also discloses orally disintegrating tablets (acronym "ODT"), comprising particles which are each formed of a particulate core containing the pharmaceutical active principle, and coated with a so-called "taste-masking" membrane comprising a mixture of polymers and of gelling substances in order to make it possible to mask the taste in the oral cavity.

Finally, from a preparation method viewpoint, manufacture of orally disintegrating tablets requires particular precautions, in particular in terms of adjustment of compression force. Indeed, if it proves to be too high, the oral breakdown time may be significantly extended, which is by definition contrary to the planned technical effect. In practice, in order to prevent this phenomenon, the compression force is often adjusted to minimal values, which has the consequence of greater mechanical fragility (friability) of such tablets in comparison to traditional tablets. Consequently, use of specific—and therefore costly—packaging such as "peelable" blisters sometimes proves necessary in order to prevent the tablet from crumbling when removed from its cell. Furthermore, again because of the compression force adjusted to minimal values, particular attention must be paid to the stability of orally disintegrating tablets over time, in particular with regard to cohesion of the tablets (also known as tablet hardness), so as to ensure that a modification does not occur during product storage, which is prone to significantly affecting the breakdown time of said tablets in the oral cavity. Furthermore, on top of these numerous drawbacks (significant time period to obtain the desired breakdown, unpleasant sensations in the mouth due to use of specific disintegrating agents, need to add masking agents, friability, possible stability problems over time, etc.), there is the high cost of the disintegrating agents used within these orally disintegrating tablets.

Patent application US 2013/0052278 discloses compositions not in the form of tablets, but in the form of orally administrable powders, which rapidly dissolve in the oral cavity. Although coming in a different galenic form to that of the orally disintegrating tablets discussed above, the compositions disclosed in US 2013/0052278 also require the presence of a disintegrating agent in their composition, so as to be able to dissolve/disintegrate in the oral cavity in a few seconds. This presents a number of drawbacks (see above), and in particular:

in economic terms, in view of the fact that such disintegrating agents generally prove expensive, but above all
in pharmacokinetic terms, because of the capacity of these disintegrating agents to increase the solubility of certain active ingredients in saliva and thereby cause a risk of per-oral absorption with the consequence of modifying the bioavailability of the active ingredient(s) contained in these compositions, which might prove particularly problematic given the reasons set out above.

Therefore the present invention is aimed at rectifying all or some of the abovementioned drawbacks.

DISCLOSURE

Therefore the object of the invention is a solid composition with rapid ingestion and facilitated swallowing, administrable to a human or animal individual, said composition being in the form of non-agglomerated solid particles, said composition comprising both the following types of particle:

Pa particles, comprising at least one active ingredient, in sufficient quantity to administer the desired dose of active ingredient to said human or animal individual (and in so doing, to obtain the planned pharmacological or nutritional effect), and Ps particles, rapidly soluble in saliva, said Ps particles being characterised by an apparent density equal to or greater than approximately 0.6 $g.cm^{-3}$ (preferably equal to or greater than 0.6 $g.cm^{-3}$), advantageously equal to or greater than approximately 0.7 $g.cm^{-3}$ (preferably equal to or greater than 0.7 $g.cm^{-3}$) and preferably between 0.7 and 1.5 $g.cm^{-3}$ inclusive;

said Ps particles being present in said composition in sufficient quantity to enable rapid ingestion and facilitated swallowing of said Pa particles in said human or animal individual.

The inventor has discovered, surprisingly, that use, in the composition in the form of non-agglomerated solid particles according to the invention, of Ps particles of high apparent density (as defined above) made it possible in particular to:

a) facilitate swallowing of the Pa particles without it being necessary for these Pa particles to be dissolved or disintegrated in saliva, without requiring exogenous water intake, thanks to a surprising effect of practically immediate dissolution of Ps particles in the salivary fluid, inducing in particular an increase in the volume thereof (allowing rapid ingestion of the Pa particles without requiring a particular swallowing effort), and b) very significantly reduce the volume of solid matter to be ingested, in particular in order to prevent product loss or cause discomfort to the patient/subject.

The person skilled in the art, learning in particular the advantage of using Ps particles of high apparent density (as defined above), will determine, without excessive difficulty and if need be with the aid of routine tests, the aforesaid "sufficient quantity" of Ps particles to include in the composition according to the invention to enable rapid ingestion and facilitated swallowing of said Pa particles by said human or animal individual.

According to a preferred embodiment of the invention, the quantity of Ps particles included in the composition according to the invention is determined by the ratio between the mass of Pa particles and the mass of Ps particles (denoted Pa/Ps), which is preferably less than 10 (10/1), preferably less than 5 (5/1), advantageously less than or equal to 4 (4/1), preferably less than or equal to 3 (3/1), and particularly preferably less than or equal to 2.5 (2.5/1). Preferably, the aforesaid mass ratio Pa/Ps is less than or equal to 1 (1/1), preferably less than or equal to 0.75 (approximately 1/1.33) and advantageously less than or equal to 0.5 (1/2).

Quite clearly, and as is well known to the person skilled in the art, the quantity of Ps particles included in the composition according to the invention may also be expressed as a mass percentage (% m) (or weight percentage, % w) in relation to the total mass of Pa and Ps particles. This may be obtained from the mass ratio Pa/Ps (of value x), by applying the following equation:

$$\%\ m\ Ps = \frac{1}{(x+1)} \times 100$$

Hence, according to the aforesaid preferred embodiment of the invention, the mass percentage of Ps particles within the composition according to the invention in relation to the total mass of Pa and Ps particles is greater than 9.09% (for example greater than 9.1%), preferably greater than 16.67% (for example greater than 17%), preferably equal to or greater than 20%, preferably equal to or greater than 25%, and particularly preferably equal to or greater than 28.57% (for example equal to or greater than 30%). Preferably, the mass percentage of Ps particles within the composition according to the invention in relation to the total mass of Pa and Ps particles is equal to or greater than 50%, preferably equal to or greater than 57.14% and advantageously equal to or greater than 66.67% (for example equal to or greater than 70%).

According to an embodiment of the invention, the mass percentage of Ps particles within the composition according to the invention in relation to the total mass of Pa and Ps particles is less than or equal to 99%.

According to a particularly preferred embodiment of the invention, the Pa particles are particles with very low solubility in saliva. In this particularly preferred embodiment of the invention, the Pa and Ps particles are "particles with differential solubility in saliva".

According to a particularly preferred embodiment of the invention, the composition comprises a homogeneous mixture of Pa and Ps particles.

Preferably, the composition is a homogeneous mixture of non-agglomerated solid particles. This homogeneous mixture of non-agglomerated solid particles is suitable for being in packed in sachets and/or sticks, preferably in single-dose sachets and/or sticks. In other words, another object of the invention is a solid composition with rapid ingestion and facilitated swallowing, comprising a homogeneous mixture of non-agglomerated solid particles, said mixture comprising, consisting primarily of, or consisting of, the two following different types of particle:

Pa particles, comprising at least one active ingredient,

Ps particles, rapidly soluble in saliva, said Ps particles having an apparent density equal to or greater than approximately 0.6 $g.cm^{-3}$ (preferably equal to or greater than 0.6 $g.cm^{-3}$), advantageously equal to or greater than approximately 0.7 $g.cm^{-3}$ (preferably equal to or greater than 0.7 $g.cm^{-3}$), and preferably between 0.7 and 1.5 $g.cm^{-3}$ inclusive.

Advantageously, the Ps particles comprise at least one polyol with low glycaemic index, such as erythritol, preferably in a mass percentage representing at least 50% of the total mass of the Ps particles.

According to a preferred embodiment, the Ps particles also comprise at least one natural organic acid, or a salt thereof, preferably a metabolically non-acidifying natural organic acid, such as citric acid and/or a salt thereof, such as calcium citrate or magnesium citrate.

Advantageously, said at least one natural organic acid, or a salt thereof, is present in the Ps particles in a mass percentage not exceeding 50% of the total mass of the Ps particles.

According to a preferred embodiment, the weight ratio of natural organic acid(s) (or a salt (salts) thereof)/polyol(s) with low glycaemic index is between 0.01 and 1 inclusive.

According to a preferred embodiment, the Ps particles have an average size of less than or equal to approximately 500 μm (preferably less than or equal to 500 μm); preferably said Ps particles have a size range of between approximately 50 μm and approximately 500 μm (preferably between 50 μm and 500 μm), preferably between approximately 100 μm and approximately 500 μm (preferably between 100 μm and 500 μm), advantageously between approximately 200 μm and approximately 400 μm (preferably between 200 μm and 400 μm).

According to a preferred embodiment, the Ps particles are free from disintegrating agents such as a cross-linked polyvinylpyrrolidone, a cross-linked carboxymethyl cellulose and/or hydroxypropyl cellulose (such as for example low-substituted hydroxypropyl cellulose comprising 7.0 to 9.9 percent by weight "hydroxypropoxyl" groups, disclosed in US 2001/0009678).

According to a preferred embodiment, the composition according to the invention is free from disintegrating agents such as a cross-linked polyvinylpyrrolidone, a cross-linked carboxymethyl cellulose and/or hydroxypropyl cellulose (such as for example low-substituted hydroxypropyl cellulose comprising 7.0 to 9.9 percent by weight "hydroxypropoxyl" groups, disclosed in US 2001/0009678).

The fact that the Ps particles and/or the composition according to the invention (advantageously both) is/are free from disintegrating agents (such as a cross-linked polyvinylpyrrolidone, a cross-linked carboxymethyl cellulose and/or hydroxypropyl cellulose) makes it possible to rectify the drawbacks presented above. In particular, it makes it possible to reduce the cost of the product and prevent potential unfavourable impacts on per-oral absorption of the active principle(s) contained in the present invention Indeed, unlike the compositions described for example in patent U.S. Pat. No. 5,464,632 or patent application US 2001/0009678, the present invention concerns a composition wherein the particles are not agglomerated and which makes it possible to obtain rapid ingestion and facilitated swallowing of the active ingredient(s) contained within the Pa particles advantageously in the absence of disintegrating agents.

According to one embodiment, the Pa particles are made up of or are coated with a hydrophobic material in order to:

protect them from moisture and/or limit their solubility in saliva, and/or modulate the release of at least one active ingredient contained therein (such as modified release, facilitated, delayed and/or targeted release) in one or more parts of the digestive tract.

Preferably, the Pa particles have an average size of less than approximately 500 µm (preferably less than 500 µm); preferably said Pa particles have a size range of between approximately 50 µm and approximately 500 µm (preferably between 50 µm and 500 µm), advantageously between approximately 100 µm and approximately 400 µm (preferably between 100 µm and 400 µm). Indeed, the Pa particles have a sufficiently "small" size to facilitate swallowing and prevent the patient/subject from being tempted to crunch up the particles, but sufficiently "big" to pour enable a good product flow.

According to a preferred embodiment, the average size of the Ps particles and the average size of the Pa particles are no more than 50%, and preferably no more than 25%, different from each other.

Another object of the invention is a medicine with rapid ingestion and facilitated swallowing or a food supplement with rapid ingestion and facilitated swallowing, for human or animal use, comprising the composition as defined previously.

Another object of the invention concerns a sachet or stick, preferably hermetically sealed, comprising:
the composition according to the invention as defined above, or
the medicine with rapid ingestion and facilitated swallowing or the food supplement with rapid ingestion and facilitated swallowing as defined above.

Another object of the invention is the use of a composition as defined above for the preparation of a medicine with rapid ingestion and facilitated swallowing or a food supplement with rapid ingestion and facilitated swallowing, for human or animal use.

Another object of the invention concerns the Ps particles as defined previously. The inventor has discovered that this composition enabled rapid ingestion and facilitated swallowing of significant weight quantities of Pa particles, typically greater than 200 mg, advantageously greater than 500 mg and possibly up to more than one gram of Pa particles within just a few seconds, without risks of oral absorption for the patient; another characteristic of said composition is coming in a compact volume. This characteristic is also particularly important since it enables all types of patients—including those afflicted by dysphagia—to easily and rapidly ingest doses of one or more active ingredient(s) greater than 200 mg and 500 mg, potentially even exceeding one gram, without risk of modification of the bioavailability of the active ingredient(s) (a consequence of oral absorption well known to the person skilled in the art as mentioned above). Surprisingly, the inventor discovered that it was not necessary for all the particles to be dissolved in the oral cavity to obtain such properties, but only a fraction thereof (Ps particles).

The combination of Pa and Ps particles, advantageously in the form of a homogeneous mixture, making it possible to ensure rapid ingestion (typically in less than 10 seconds and advantageously in less than 5 seconds) and without a particular swallowing effort (facilitated swallowing), is also simple to prepare, which represents a certain asset. Indeed, this mixture in particular does not need to be pre-compressed to be administered to the patient/subject. This makes it possible, among other things, to overcome the problems of friability and stability over time which are inherent in the orally disintegrating tablets from the prior art (see above). Due to the high apparent density of the Ps particles, this homogeneous mixture comes in a minimal volume, which enables the patient to easily ingest significant quantities of active ingredient, typically greater than 200 mg, very rapidly (namely without it being necessary to observe a specific breakdown time) and without requiring the use of a disintegrating agent (also known as "super-disintegrating agent"), which represents a definite saving and reduces the risk of observing a modification of bioavailability due to the phenomenon of per-oral absorption, as explained above.

As stated previously, the composition according to the invention comes in the form of a mixture of non-agglomerated particles, said particles not being agglomerated to each other ("free" or "non-cohesive" particles), as opposed to galenic forms comprising particles agglomerated together such as compressed solid forms.

According to an embodiment of the invention, the particles flow freely when, for example, the European Pharmacopoeia's so-called "funnel" test (see European Pharmacopoeia 8.0, "2. Analytical methods", 2.9.16) is performed, on a sample of the composition according to the invention. In the context of this "funnel" test, it is considered that the particles flow freely if, when this test is implemented, a typical flow of 100 g of sample is obtained in less than 20 seconds, preferably in less than 10 seconds.

Furthermore, said particles possess, optimally, size and apparent density characteristics which give them suitable flow properties and a low volatility so as to facilitate manufacturing of the product and reduce inhalation risks for the manufacturing preparer/operative and/or the patient/subject. That is why, according to a preferred embodiment of the invention, said composition comprises multiple non-agglomerated particles, suitable for being packed in sachets and/or sticks (preferably in single-dose sachets and/or sticks)).

Advantageously, the Ps and Pa particles do not need to be compressed together, even to form other free particles, which facilitates preparation of the composition according to the invention and prevents use of a disintegrating agent(s) within said composition.

In summary, the solid composition with rapid ingestion and facilitated swallowing according to the invention proves to be particularly advantageous, insofar as said composition:
is easy to prepare,
makes it possible to overcome the problems of friability, breakdown time and stability over time encountered with the orally disintegrating tablets from the prior art (such as those disclosed in US 2001/0009678 and WO 2006/047493),
allows rapid ingestion and facilitated swallowing of large weight quantities of particles comprising at least one active ingredient, without it being necessary to observe a specific breakdown time for the Pa particles to be dissolved or disintegrated.
is administrable to all types of patient (including those affected by dysphagia),
proves to be more economic than orally disintegrating tablets—such as those disclosed in US 2001/0009678 and WO 2006/047493—requiring the presence of expensive disintegrating agents,
makes it possible to limit the risk of observing a modification of the bioavailability of the active ingredient because of the phenomenon of per-oral absorption, and
makes it possible to prevent an unpleasant sensation in the mouth.

Definitions

Solid composition with rapid ingestion and facilitated swallowing. "Solid composition with rapid ingestion and facilitated swallowing" is taken to mean, in the sense of the present invention, a solid composition enabling:

rapid ingestion such that the maximum oral dwell time does not exceed 10 seconds in the oral cavity and is advantageously less than 5 seconds, facilitated/easy swallowing, said swallowing being facilitated by solubilisation of the Ps particles (see definition below) in saliva, inside the oral cavity. Indeed, the inventor has discovered, against all expectation, that the solubilisation/dissolution of Ps particles in saliva resulted in a rapid increase in salivary volume, with the effect of enabling ingestion of the Pa particles (see definition below), without any particular swallowing effort and without it being necessary for said Pa particles to be dissolved in saliva.

Particle. The term "particle" designates a solid, discrete, small-sized element comprising one or more substances. In the context of the invention, this size is preferably less than 1 mm and greater than 0.05 mm, in particular in order to:

i) prevent excessively fine particles from being inhaled by the manufacturing preparer/operative and/or the patient/subject, and ii) facilitate product preparation while limiting air-borne contamination in the manufacturing workshops.

Reference test for determining particle solubility in saliva. Particle solubility in saliva is determined as follows: 500 mg of particles are placed in a 5 mL volume of water for a predetermined time (for example, 10 seconds, 20 seconds or 30 seconds) under gentle stirring at 37° C. A suitable determination protocol consists for example in placing 500 mg of Ps particles or Pa particles in a test tube pre-filled with 5 mL of water at 37° C. and stirring the test tube with a Vortex type stirrer for a predetermined time (for example, 10 seconds, 20 seconds or 30 seconds). In case of partial dissolution or absence/near-absence of dissolution (for example in the case of Pa particles), any undissolved particles are collected on a filter. Any undissolved particles are oven-dried at approximately 40° C. and then weighed. Then the mass fraction of dissolved particles is determined by applying the formula below:

(initial mass of particles−weighed mass of undissolved particles)/initial mass of particles.

Quite clearly, the percentage mass is obtained by multiplying the mass fraction by 100.

Ps particles. "Ps particles" is taken to mean, in the sense of the present invention, particles rapidly soluble in saliva characterised in that, when the "reference test to determine particle solubility in saliva" described above is applied, more than 50%, preferably more than 75%, advantageously more than 90%, and preferably 100%, of the initial mass of particles is solubilised/dissolved in saliva in less than 30 seconds, preferably in less than 20 seconds, advantageously in less than 10 seconds, and particularly preferably in less than 5 seconds. Such a solubilisation/dissolution is generally known as "quasi-immediate" solubilisation or "quasi-immediate" dissolution.

The inventor has discovered that these Ps particles, of high apparent specific gravity/density, made it possible in particular to facilitate swallowing of the Pa particles (see definition below), without it being necessary for these Pa particles to be dissolved or disintegrated in saliva. This is obtained by a surprising effect of quasi-immediate dissolution of the Ps particles in the salivary fluid, inducing in particular an increase in the volume thereof (allowing rapid ingestion of the Pa particles without needing any particular swallowing effort).

According to a particularly preferred embodiment, the aforesaid Ps particles (also known as with "quasi-immediate dissolution in saliva" or also with "quasi-immediate solubilisation in saliva") are characterised by a sufficiently high apparent density, so as to very significantly reduce the volume of solid matter to be ingested. This is a particularly important characteristic of the invention since the composition which is the object of the present invention is designed to be introduced directly into the mouth (preferably on the tongue) of the person wishing to ingest the active ingredient, and then directly swallowed by them without needing exogenous water intake (such as a glass of water). Consequently, the volume of said composition to be ingested should advantageously be as small as possible in order to facilitate swallowing. Indeed, if the volume of particles is too great, it will be hard to introduce the whole of it onto the tongue of the patient/subject without a risk of product loss or there is a risk of causing discomfort for the patient/subject.

The high apparent density of Ps particles makes it possible to very significantly reduce the volume of dry matter to be ingested. As stated previously, Ps particles have a high apparent density, namely equal to or greater than approximately 0.6 g.cm$^{-3}$, advantageously equal to or greater than approximately 0.7 g.cm$^{-3}$, and preferably between 0.7 and 1.5 g.cm$^{-3}$ inclusive.

According to a preferred embodiment, these Ps particles have an average size of less than or equal to 500 μm (advantageously less than 500 μm). Preferably, these Ps particles have a size range of between 100 μm and 500 μm, advantageously between 200 μm and 400 μm, in order to facilitate swallowing the product. These Ps particles (like Pa particles for that matter) preferably have an average size of greater than 50 μm in order to have sufficient pourability to facilitate the manufacture and use of the composition according to the invention and/or prevent any risk of inhalation by the manufacturing preparer and/or the subject/patient, for example when opening the packaging (also an important characteristic to take into account). This sufficient pourability is determined/evaluated by implementing, for example, the European Pharmacopoeia's so-called "funnel" test (see European Pharmacopoeia 8.0, "2. Analytical methods", 2.9.16). As is known to the person skilled in the art, this "funnel" test makes it possible to qualify pourability as being "sufficient", if, when this test is implemented, a flow of 100 g of sample is obtained in less than 20 seconds, preferably in less than 10 seconds.

According to a preferred embodiment, the Ps particles do not contain a disintegrating agent such as a cross-linked polyvinylpyrrolidone, a cross-linked carboxymethyl cellulose and/or hydroxypropyl cellulose (such as for example low-substituted hydroxypropyl cellulose comprising 7.0 to 9.9 percent by weight "hydroxypropoxyl" groups, disclosed in US 2001/0009678). In fact, the composition developed by the inventor makes it possible to overcome the need to use such disintegrating agents and the drawbacks associated with them (see above).

According to an embodiment of the invention, Ps particles may contain other compounds making it possible to improve the manufacture or obtain a more pleasant taste, such as sweeteners preferably of natural origin such as extracts of *Stevia rebaudiana* or flavourings suitable for human or veterinary use, preferably of natural origin, such as plant extracts (for example orange, lemon, grapefruit, strawberry, raspberry, cranberry, redcurrant, blueberry, blackcurrant, mint . . . ) with a view to improving the taste perception of the composition comprising these Ps particles.

Ps particles may be prepared via conventional techniques such as granulation, extrusion, crystallisation, nebulisation, beading and may, if applicable, be coated with an external shell.

Particle size. In order to characterise the particle size, use is made of, for example, a granulometric analysis by means of sieving, which is a traditional method described in the European Pharmacopoeia using a column of sieves of decreasing size subjected to a mechanical vibration system, making it possible for the particles to be distributed by size on the different sieves. After weighing the quantities of particles on each sieve, the results can be expressed in the form of a size histogram or it is possible to indicate the proportion of particles greater than or less than a given size (sieve mesh). For example using this principle, it will be possible to express the percentage of particles less than 1000 µm, 710 µm, 500 µm, 355 µm, 250 µm, 180 µm 125 µm, 90 µm for the arithmetic progressions described in the Pharmacopoeia.

Polyol(s) with low glycaemic index. According to a particularly preferred aspect of the invention, the Ps particles according to the invention comprise at least one (preferably one) polyol with low glycaemic index, preferably erythritol ((2R,3S)-butane-1,2,3,4-tetraol; CAS No.: 10030-58-7). "Polyol(s) with low glycaemic index" is taken to mean, in the sense of the present invention, a compound which, once ingested in the body, does not increase the glucose level in the blood plasma by more than 15 compared to a glucose control value (set by definition at 100). Other polyols with low glycaemic index which can be used within the composition according to the invention are for example, mannitol, lactilol, sorbitol, xylitol, iso-maltilol (or possibly maltitol).

Advantageously, the polyol with low glycaemic index, such as erythritol, is present in the Ps particles in a mass percentage representing at least 50% of the total mass of the Ps particles.

Particularly advantageously, use of the Ps particles comprising at least once polyol with low glycaemic index makes it possible to confer on the preparation taste properties, such as a pleasant taste, which enables one or more grams of product to be taken orally.

Furthermore, use of Ps particles comprising at least one polyol with low glycaemic index—and preferably erythritol—also makes it possible to obtain compositions potentially suitable for all types of subjects, in particular those who must monitor their glycaemic index for medical reasons (diabetic subjects). This represents a significant advantage.

Natural organic acid. Particularly advantageously, Ps particles comprise, are essentially composed of, or are composed of at least one polyol with low glycaemic index, as stated previously, and at least one natural organic acid, such as citric acid, or a salt thereof. "Natural organic acid" is taken to mean, in the sense of the present invention, an organic acid (carbon-based) naturally present in the animal or plant kingdom and compatible for pharmaceutical or nutritional use.

As natural organic acids, mention may in particular be made of (non-exhaustive list):
hydrosoluble, such as citric, malic, tartric, lactic, glycolic, oxalic, salicylic, carbonic, formic, acetic, or propionic acid;
including natural amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine;
non-hydrosoluble belonging to the saturated fatty acids family such as butyric, caprylic, capric, lauric, myristic, palmitic, stearic, arachidic, behenic, cerotic, lignoceric acid; and
non-hydrosoluble belonging to the unsaturated fatty acids family such as oleic, linoleic, linolenic, arachidonic or eicosapentaenoic acid.

Use of this organic acid within the Ps particles according to the invention proves particularly advantageous in that it makes it possible in particular to obtain an increase in salivary volume (or even potentialise the increase in salivary volume induced by quasi-immediate dissolution of the Ps particles in saliva), which aids swallowing of the Pa particles.

Non-acidifying natural organic acid. Advantageously, the natural organic acid is selected from the so-called "non-acidifying" natural organic acids, i.e. an acid which possesses a negative value according to the PRAL index (Potential Renal Acid Load, as determined by the experimental work of Doctor Thomas Remer): REMER T, MANZ F, ["Potential renal acid load of foods and its influence on urine pH", *J Am Diet Assoc.* 1995 July; 95(7):791-7].

This index, which is expressed in milliequivalents (mEq), evaluates the acid (or alkaline) load generated in the body by a food or meal. This makes it possible to better adhere to the acid-base equilibrium of the patient/subject, in whom a modern diet generally tends to cause acid overloads (positive value of the PRAL index). Such acids are for example chosen from the group consisting of citric acid, and the salts thereof, such as calcium citrate or magnesium citrate.

Preferably the natural organic acid, such as citric acid, or a salt thereof, is present in the composition of the Ps particles in a proportion not exceeding 50% by mass of said Ps particles.

The weight ratio of natural organic acid (or a salt thereof)/polyol(s) with low glycaemic index is advantageously between 0.01 and 1 inclusive.

As stated previously, the Ps particles may be prepared via conventional techniques such as granulation, extrusion, crystallisation, nebulisation, beading and may, if applicable, be coated with an external shell. In particular, to prepare Ps particles comprising a polyol with low glycaemic index and a natural organic acid (or a salt thereof), it is possible to solubilise the compounds in a suitable solvent and then evaporate the solvents, for example via a nebulisation and drying technique.

Pa particles. The Pa particles comprise the active ingredient and generally an excipient. According to a particularly preferred embodiment of the invention, the Pa particles are particles with very low solubility in saliva (salivary fluid). Indeed, insofar as, unlike certain compositions in the form of powders from the prior art (see in particular US 2013/0052278, discussed above), it is neither necessary, nor desirable, for Pa particles (containing the active ingredient(s)) to be dissolved/solubilised in saliva. "Particles with very low solubility in saliva" is taken to mean particles which, when the "reference test for determining particle solubility in saliva" defined previously is applied, are characterised in that less than 10%, advantageously less than 5%, of the mass of the active ingredient(s) which they contain is dissolved in saliva after 10 seconds. Advantageously, less than 10%, advantageously less than 5%, of the mass of the active substance(s) that they contain is dissolved in the salivary fluid after 30 seconds.

According to a preferred embodiment, Pa particles make it possible to confer on the active ingredient(s) that they contain particular properties, for example:

i) when preparing the product or storing the product, such as properties in terms of moisture protection, and ii) after ingestion of the product, such as modified release properties (for example facilitated, delayed or targeted release in one or various parts of the digestive tract). Such particles are known as "functional Pa particles", such that one of the objects of the present invention is to enable rapid ingestion and facilitated swallowing of functional Pa particles.

In order to promote homogeneity of the mixture, the average size of the Pa particles is generally chosen from a range of 50 μm to 500 μm, advantageously from 100 μm to 400 μm. According to a particular embodiment, the chosen range is 150 μm to 300 μm, in order to facilitate swallowing of the product and advantageously slightly less than the average size of the Ps particles, in order to limit the risks of abrasion during distribution operations of the product.

Pa particles may be prepared via conventional techniques such as granulation, extrusion, crystallisation, nebulisation, beading and may, if applicable, be coated with an external shell. This may be for example a) a lipophilic compound preferably of plant origin, such as a natural fatty acid such as stearic acid, palmitic acid, oleic acid or an ester thereof based on glycerol, sorbitol, or macrogols or b) a protein or a polymer for food or pharmaceutical use such as b.1) a protein or polymer which is natural or modified for example based on cellulose, starch, alginate, xanthan, carrageenan or b.2) a synthetic polymer for example derived from acrylic, methacrylic, vinylic, lactic, glycolic acid or amino acids, or obtained by condensation of ethylene oxide, or propylene oxide, and/or various combinations thereof.

Ratio between Pa and Ps particles. The ratio between the quantity of particles Pa and Ps depends on factors such as in particular the final volume of the composition according to the invention, on the dose of active ingredient to be administered and on the dissolution sensation that is being sought. As stated above, the ratio between the mass of Pa particles and that of Ps particles according to the invention is preferably less than 10 (10/1), preferably less than 5 (5/1), advantageously less than or equal to 4 (4/1), preferably less than or equal to 3 (3/1), and particularly preferably less than or equal to 2.5 (2.5/1). Preferably, said mass ratio Pa/Ps is less than or equal to 1 (1/1), preferably less than or equal to 0.75 (approximately 1/1.33) and advantageously less than or equal to 0.5 (1/2).

It is advantageous to choose Ps particles and Pa particles of close or similar granulometries, in order to facilitate the homogeneity of the mixture of Pa and Ps particles. Hence it is for example advantageous, in the sense of the present invention, to use Ps and Pa particles with average sizes not differing by more than 50% and advantageously by no more than 25% from each other. Indeed, it proves particularly advantageous for the Ps and Pa particles to come in relatively close sizes so as to ensure the homogeneity of the final mixture.

Homogeneous. The qualifying adjective "homogeneous" is used, within the present patent application, in order to characterise the mixture of particles according to the invention by defining a sufficiently uniform distribution of the mixture particles. Hence, according to a preferred embodiment, the mixture of particles according to the invention is considered "homogeneous" if, within various sampling operations (generally 3 to 6 samples) performed during preparation of the product in various parts of the mixer in said mixture (for example 3 samples of at least 1 g each in the mixer in the vertical axis [top centre, middle centre and bottom centre]), the active ingredient is in proportions adhering to the theoretical formula of the final mixture with tolerated variations (variation coefficients) of up to 10% and advantageously tolerated variations of up to 5%. Note that by way of example, the active ingredient is dosed in each sampling operation by a liquid phase chromatography technique, well known to the person skilled in the art.

Active ingredient. "Active ingredient" is taken to mean, in the sense of the present invention, any molecule or any assembly of molecules capable of making modifications or modulations to the operation of a biological system. Depending on the envisaged use, this active ingredient may be:

a pharmaceutical active ingredient (also known as "pharmaceutical active principle"; suitable for forming part of the composition of a medicine), namely, which is designed to be ingested orally, an active ingredient for cosmetic purposes (also known as "cosmetic active principle"), namely a non-medicinal active ingredient designed for body care and beauty (for example a molecule or set of molecules used for slimming, preventing or slowing cutaneous ageing or even improving the appearance of the skin), a nutritional ingredient, namely at least one nutrient or a substance with nutritional or physiological effect; this nutritional ingredient is suitable for preparing a food supplement/a nutritional composition, or also a veterinary active ingredient.

By way of illustration (though non-limiting), it is possible to envisage, as active ingredient(s), the active principles used in the pharmacological classes such as Allergy, Anaesthesia, Sedation, Treatment of pain and inflammation, Cancerology haematology, Cardiology Angiology, Contraception and pregnancy interruption, Dermatology, Endocrinology, Gastro-Entero-Hepatology, Gynaecology, Haemostasis, Immunology, Infectiology, Parasitology, Metabolism, Nutrition, Neurology-psychiatry, Ophthalmology, Otorhinolaryngology, Pneumology, Diagnostic products or other treatment products, Rheumatology, Blood and derivatives, Stomatology, Toxicology, Urology, Nephrology, etc.

More precisely, and again for illustrative purposes, it is possible to envisage, as active ingredient(s), the active principles used in the following pharmacological classes:

Molecules used as anti-allergens: alimemazine, cetirizine, desloratadine, diphenhydramine doxylamine, fexofenadine, hydroxyzine, loratadine, mepyramine, promethazine, terfenadine;

Molecules with analgesic, antalgic, sedative and anti-inflammatory properties: acepromazine, alprazolam, amitriptyline, barbital, bromazepam, chlorpromazine, codeine, dextrometorphan, fentanyl, haloperidol, imipramine, lorazepam, midazolam, morphine, naloxone, oxomemazine, phenobarbital, sulpiride, tetrazepam, zolpidem, zopiclone, alfentanyl, buprenorphine, codethyline, dextropropoxyphene, morphine, pavot, pentazocine, sufentanil, tapentadol, tramadol, acetylsalicylic acid, betamethasone, cortisone, dexamethasone, diclofenac, hydrocortisone, ibuprofen, ketoprofen, naproxen, piroxicam, paracetamol, prednisolone, tiaprofenic acid, triamcinolone codeine, morphine, tramadol;

Antineoplastic molecules: carboplatin, cisplatin, docetaxel, doxorubicin, etoposide, irinotecan, methotrexate, placlitaxel, thiotepa, vincristine;

Molecules used for cardiovascular system disorders: alprenolol, captopril, clopidogrel, digoxin, enalapril, felodipine, furosemide, heptaminol, nadolol, olmesartan, propanolol, ramipril, telmisartan, trinitrine, valsartan, verapamil;

Sex hormones and modulators: desogestrel, levonorgestrel, progesterone, estradiol, ethinylestradiol, danazol;

Molecules used in dermatology or dermocosmetics: acitretin, isotretinoin, retinoic acid and derivatives, omega-3-type polyunsaturated fatty acids;

Molecules used in endocrinology: carbimazole, levothyroxine, thiamazole;

Molecules used in gastro-entero-hepatology: aluminium carbonate, calcium carbonate, loperamide, racecadrotil, domperidone, ondansetron, cimetidine, esomeprazole, omeprazole, pantoprazole, hyoscine, mebeverine, lactulose, bisacodyl, senna, enoxolone, troxipide, cisapride, metoclopramide, alverine;

Molecules used for modulating immune response: azathioprine, cyclosporine, mycophenolic acid and salts, sirolimus, tacrolimus;

Molecules used in infectiology and parasitology: aciclovir, atazanavir, efavirenz, ganciclovir, indinavir, lamivudine, maraviroc, saquinavir, zidovudine, chloroquine, mefloquine, quinine, albendazole, fenbendazole, metronidazole, ivermectin, levamisole, niclosamide, praziquantel, amikacin, neomycin, ethambutol, rifamycin, cephalexin, ceftiofur, imipenem, chloramphenicol, vancomycin, clindamycin, azithromycin, erythromycin, amoxicillin, oxacillin, levofloxacin, orfloxacin, sulfanilamide, sulfathiazole, tetracycline, fosfomycin, amphotericin B, fluconazole, itraconazole, ketoconazole, miconazole;

Molecules used in metabolic disorders and nutrition: acarbose, metformin, sitagliptin, glibenclamide, glicazide, tolbutamide, allopurinol, colchicine, probenecid, alendronic acid and derivatives, hydrosoluble vitamins such as group B vitamins, vitamin C, liposoluble vitamins (A,D,E,K), minerals (such as Calcium, Magnesium, Zinc in the form of various salts);

Molecules used in neurology and psychiatry: amantadine, bromocriptine, entacapone, levodopa, selegiline, sumatriptan, almotriptan, naratriptan, carbamazepine, clonazepam, ethosuximide, gabapentin, lamotrigine, levetiracetam, phenytoin, topiramate, valproate, amitriptyline escitalopram, fluoxetine, imipramine, mirtazapine, phenelzine, trazodone, venlafaxine;

Molecules used for respiratory disorders: aminophylline, caffeine, formoterol, montelukast, theophylline, acetylcysteine, carbocysteine, dextromethorphan, xylometazoline;

Molecules used as antidotes, antagonists or chelating agents: activated charcoal, dimercaprol, naloxone, penicillamine, edetic acid and derived salts;

Molecules used in urology: finasteride, oxybutynin, papaverine, sildenafil, tadalafil, tamsulosin.

Plant extracts used in various indications such as extracts of *Curcuma longa, Boswellia serrata, Tagetes erecta, Zingiber officinale, Whitania somnifera, Allium sativum, Aloe vera, Illicum anisum, Borrago officinalis, Matricaria chamomilla, Sylbum marianum, Coriandrum sativum, Digitalis purpurea, Eucalyptus globulus, Ficus carica, Gingko biloba, Althaea officinalis, Plantago ovata, Hypericum perforatum, Myrtus communis, Vaccinium macrocarpon, Capsicum annuum, Vitis vinifera, Glycyrrhiza glabra, Salix alba, Spirulina, maxima, Valeriana officinalis.*

It is also possible to envisage, as active ingredient(s), micro-organisms such as probiotics (*Lactobacillus acidophilus, Lactobacillus casei, Lactobacillus reuteri, Lactobacillus plantarum, Saccharomyces boulardii, Saccharomyces cerevisiae, Bifidobacterium longum, Bifidobacterium infantis, Bifidobacterium breve* . . . ).

Apparent density (or "bulk density"). As is well known to the person skilled in the art, the apparent density of a powder is taken to be the density of said powder not subjected to a compaction force and comprises the volume of the particles, the inter-particle volume and the volume of the particle pores. For more clarification in this respect, the person skilled in the art may refer, if applicable, to the definition of "bulk density" given in the European Pharmacopoeia (see European Pharmacopoeia 8.0, "2. Analytical methods", 2.9.34, page 367). Preferably, the apparent density is determined by implementing the so-called "graduated test tube" reference method, designated as "method 1" in point 2.9.34 of European Pharmacopoeia 8.0 (page 367). Said "graduated test tube" method consists in determining the apparent density by measuring the volume occupied by a known mass of powder poured into a graduated cylinder (such as a graduated test tube of sufficient precision) after passing through a sieve (with mesh opening of at least 1.0 mm) and according to the following procedure: 100 grams of powder to be examined is introduced in a dry graduated test tube of sufficient pressure, without compacting. The reading of the volume occupied by the powder on the test tube graduation represents the apparent density normally estimated to the nearest 2 mL. For more clarification, the person skilled in the art may refer, if applicable, to point 2.9.34 of European Pharmacopoeia 8.0 (page 367), entitled "METHOD 1: GRADUATED TEST TUBE". Methods other than the so-called "graduated test tube" may be used to determine the apparent density of the composition in the form of non-agglomerated solid particles according to the invention, such as the so-called "weighing bottle" method—designated as "method 3" in point 2.9.34 of European Pharmacopoeia 8.0 (pages 367 and 368)—or also the so-called "volumeter" method (designated as "method 2" in point 2.9.34 of European Pharmacopoeia 8.0 (page 367); with the European Pharmacopoeia favouring said methods 1 and 3.

DETAILED DESCRIPTION

The examples presented below make it possible to better illustrate the present invention. However, these examples must under no circumstances be regarded as limiting the scope of said invention in any way.

EXAMPLES

Example 1

Preparation of One Kilogram (1 kq) of Food Supplement Based on Zinqiber Officinale Composed of a Homogeneous Mixture of Pa and Ps Particles 10% by weight Pa particles and 90% by weight Ps particles are introduced into a rotary drum mixer, and are stirred for 15 minutes to form a homogenous mixture of white to white-cream coloured particles.

Pa particles: The Pa particles are made up of a mixture of 40% extract of Zingiber officinale (ginger) root and 60% sorbitol monostearate, and prepared according to a beading technique (technique of nebulisation followed by cooling) well known to the person skilled in the art, in order to limit their solubility in the oral cavity. Therefore the Pa particles present very low solubility in saliva (inside the oral cavity): indeed, a quantity less than 5% of the mass of the active ingredient, gingerol, is dissolved after 10 seconds when the "reference test for determining particle solubility in saliva" defined above is applied, so as not to cause in particular an excessively spicy sensation in the patient's mouth. Granulometric analysis of the Pa particles according to the sieving method shows that more than 90% of them are less than 500 µm in size and less than 10% are less than 125 µm in size.

Ps particles: The Ps particles are made up of a mixture of 99% erythritol and 1% citric acid, and are obtained by mixing in solution and then drying. The particles present an apparent density of between 0.7 and 0.8 g.cm$^{-3}$ inclusive, and rapid solubilisation in saliva—in less than 20 seconds—when the "reference test for determining particle solubility in saliva" defined above is applied. Granulometric analysis of the Ps particles according to the sieving method shows that more than 90% of them are less than 710 pm in size and less than 10% are less than 125 µm in size. The homogeneity of the mixture thus formed is assessed by taking 3 samples of at least 1 g from the mixer in the vertical axis (top centre, middle centre, bottom centre) and assaying one of the active ingredients (gingerol) via a conventional liquid chromatography technique. The results obtained are set out in table 1 below and show a variation coefficient of less than 5%.

TABLE 1

| Sample | Dosage (mg) |
| --- | --- |
| Top | 188 |
| Middle | 174 |
| Bottom | 178 |
| Mean | 180 |
| Standard deviation | 7.21 |
| VC | 4.01% |

This variation coefficient, of less than 5%, confirms that the mixture of Pa and Ps particles is homogeneous, as stated previously.

The mixture thus obtained is particularly homogeneous and dense due to the high apparent density and/or the specific granulometry of the Ps particles (of between 0.1 and 1 millimetre). Furthermore, since the average particle size is more than 50 µm, it facilitates the preparation operations by limiting particle dissemination during the manufacturing operations, as well as the risk of inhalation of the product by the user when opening and taking the product.

In addition, said mixture possesses sufficient pourability (measured via the European Pharmacopoeia's so-called "funnel" test (see European Pharmacopoeia 8.0, "2. Analytical methods", 2.9.16) which enables it to be packed and taken directly into the user's mouth (oral administration) without requiring exogenous water intake or a prior step of dilution in a glass of water.

The homogeneous mixture of Pa and Ps particles proves particularly stable in particular because of its preparation method, which makes it possible to separately prepare the Pa particles, on the one hand, and Ps particles on the other.

Example 2

Preparation of One Kilogram (1 kg) of Food Supplement Based on Vaccinum Macrocarpon Composed of a Homogeneous Mixture of Pa and Ps Particles 40% by weight Pa particles and 60% by weight Ps particles are introduced into a rotary drum mixer, and are stirred for 15 minutes to form a homogenous mixture of particles.

Pa particles: The Pa particles are made up of a mixture of 40% extract of Vaccinium macrocarpon (cranberry) and 60% glycerol monostearate, and prepared according to a beading technique (technique of nebulisation followed by cooling) well known to the person skilled in the art, in order to limit their solubility in the oral cavity. Therefore the Pa particles present very low solubility in saliva (inside the oral cavity): indeed, a quantity less than 5% of the mass of the active ingredient (proanthocyanidins or PACs) is dissolved after 10 seconds when the "reference test for determining particle solubility in saliva" defined above is applied, so as not to cause in particular excessive acidity in the patient's mouth. Granulometric analysis of the Pa particles according to the sieving method shows that more than 90% of them are less than 500 µm in size and less than 10% are less than 125 µm in size.

Ps particles: The Ps particles are made up of a mixture of 98.5% erythritol and 1.5% citric acid, and are obtained by granulation and then drying. The particles present an apparent density of around 0.8 g.cm$^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 µm in size and less than 10% are less than 125 µm in size.

Example 3

Preparation of One Kilogram (1 kq) of Food Supplement Based on Tagetes Erecta Composed of a Homogeneous Mixture of Pa and Ps Particles 20% by weight Pa particles and 80% by weight Ps particles are introduced into a rotary drum mixer, and are stirred for 15 minutes to form a homogenous mixture of particles.

Pa particles: The Pa particles are made up of a mixture of 40% Tagetes erecta extract (lutein), 40% microcrystalline cellulose and 20% hypromellose (hydroxypropyl methylcellulose), and prepared according to a granulation technique followed by film-coating on a fluid air bed well known to the person skilled in the art, in order to improve their stability. The Pa particles also present low solubility in saliva (in the oral cavity) according to the "reference test for determining particle solubility in saliva" defined above, so as not to cause an excessively pronounced taste in the patient's mouth. Granulometric analysis of the Pa particles according to the sieving method shows that more than 90% of them are less than 500 µm in size and less than 10% in size are less than 125 µm.

Ps particles: The Ps particles are made up of a mixture composed of 60% sorbitol, 20% erythritol, 18% tricalcium citrate and 2% citric acid, and are obtained by granulation and drying. The particles present an apparent density of around 0.8 g.cm$^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 µm in size and less than 10% are less than 125 µm in size.

Example 4

Preparation of One Kilogram (1 kg) of Food Supplement Based on Chlorella and Carbo Vegetalis Composed of a Homogeneous Mixture of Pa and Ps Particles 70% by weight of a mixture of Pa particles and 30% by weight Ps particles are introduced into a rotary drum mixer, and are stirred for 15 minutes to form a homogenous mixture of particles.

Mixture of Pa particles: this mixture comprises equal parts of:

- Pa1 particles, made up of 40% Chlorella and 60% sorbitol monostearate, and
- Pa2 particles, made up of 40% Carbo vegetalis (vegetable carbon) and 60% sorbitol monostearate;
- said Pa1 and Pa2 particles being prepared according to a beading technique (nebulisation followed by cooling) well known to the person skilled in the art, in order to limit dissemination in the oral cavity of the active ingredients. Therefore the Pa particles present very low solubility in saliva (inside the oral cavity) according to the "reference test for determining particle solubility in saliva" defined above, so as not to cause, in particular, dissemination and coloration of the mucous membranes and the patient's mouth. Granulometric analysis of the Pa particles according to the sieving method shows that more than 90% of them are less than 500 μm and less than 10% are less than 125 μm.

Ps particles: The Ps particles are made up of a mixture of 70% erythritol and 28% xylitol, and 2% citric acid, and are obtained by mixing in solution and then drying. The particles present an apparent density of around 0.8 $g.cm^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 μm in size and less than 10% are less than 125 μm.

Example 5

Preparation of One Kilogram (1 kg) of Pharmaceutical Preparation Based on Ibuprofen Composed of a Homogeneous Mixture of Pa and Ps Particles 50% by weight Pa particles and 50% by weight Ps particles are introduced into a rotary drum mixer, and are stirred for 15 minutes to form a homogenous mixture of particles.

Pa particles: The Pa particles are made up of a mixture of 80% ibuprofen and 20% sorbitol monostearate, and prepared according to a hot melt coating technique well known to the person skilled in the art, in order to prevent direct contact between the ibuprofen and the patient's oral mucosa. Therefore the Pa particles present very low solubility in saliva (inside the oral cavity): indeed a quantity of less than 5% of the mass of active ingredient ibuprofen is dissolved after 10 seconds when the "reference test for determining particle solubility in saliva" defined above is applied, so as to prevent local irritation as well as a risk of absorption via the oral mucosa. Granulometric analysis of the Pa particles according to the sieving method shows that more than 90% of them are less than 500 μm in size and less than 10% are less than 125 μm in size.

Ps particles: The Ps particles are made up of a mixture composed of 90% erythritol, 9% tricalcium citrate and 1% citric acid, and are obtained by granulation. The particles present an apparent density of around 0.8 $g.cm^{-3}$, and rapid solubilisation in saliva in accordance with the "reference test for determining particle solubility in saliva" defined above. Granulometric analysis of the Ps particles according to the sieving method shows that more than 90% of them are less than 710 μm in size and less than 10% are less than 125 μm.

Example 6

Preparation of One Kilogram (1 kg) of Pharmaceutical Preparation Based on 5 ASA (5 Aminosalicylic Acid) Composed of a Homogeneous Mixture of Pa and Ps Particles 70% by weight Pa particles and 30% by weight Ps particles are introduced into a rotary drum mixer, and are stirred for 15 minutes to form a homogenous mixture of particles.

Pa particles: The Pa particles are made up of a mixture of 80% 5-ASA and 20% a pharmaceutical grade methacylic polymer insoluble in acid medium, and prepared according to a technique of film coating technique on a fluid air bed (FAB) well known to the person skilled in the art, in order to prevent direct contact between the 5 ASA and the patient's oral mucosa. Therefore the Pa particles present a very low solubility in saliva (inside the oral cavity) according to the "reference test for determining particle solubility in saliva" defined above, and enable a gradual release of the active substance (5ASA) into the digestive tube (colon) in order to obtain optimum efficacy. Granulometric analysis of the Pa particles according to the sieving method shows that more than 90% of them are less than 500 μm in size and less than 10% are less than 125 μm in size.

Ps particles: The Ps particles are made up of a mixture composed of 90% erythritol, 9% tricalcium citrate and 1% citric acid, and are obtained by granulation. The particles present an apparent density of around 0.8 $g.cm^{-3}$, and rapid solubilisation in saliva according to the "reference test for determining particle solubility in saliva" defined above. Granulometric analysis of the Ps particles according to the sieving method shows that more than 90% of them are less than 710 μm in size and less than 10% are less than 125 μm.

Example 7

Preparation of One Kilogram (1 kq) of Food Supplement Based on Curcuma Longa Composed of a Homogeneous Mixture of Pa and Ps Particles 50% by weight Pa particles and 50% by weight Ps particles are introduced into a rotary drum mixer, and are stirred for 15 minutes to form a homogenous mixture of particles.

Pa particles: The Pa particles are made up of a mixture of 75% Curcuma Longa extract and 25% sorbitol monostearate, and prepared according to a hot melt coating technique well known to the person skilled in the art, in order to prevent direct contact between the plant extract and the patient's oral mucosa. Therefore the Pa particles present very low solubility in saliva (inside the oral cavity): indeed a quantity less than 5% of the mass of the active ingredient (curcumin) is dissolved after 10 seconds when the "reference test for determining particle solubility in saliva" defined above is applied, so as to prevent in particular coloration of the oral mucosa. Granulometric analysis of the Pa particles according to the sieving method shows that more than 90% of them are less than 710 pm in size and less than 10% are less than 125 µm in size.

Ps particles: The Ps particles are made up of a mixture composed of 99% erythritol and 1% citric acid, and are obtained by granulation. The particles present an apparent density of around 0.8 g.cm$^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 µm in size and less than 10% are less than 125 µm in size.

Example 8

Preparation of One Kilogram (1 kg) of Food Supplement Based on Boswellia Serrata Composed of a Homogeneous Mixture of Pa and Ps Particles 40% by weight Pa particles and 60% by weight Ps particles are introduced into a rotary drum mixer, and are stirred for 15 minutes to form a homogenous mixture of particles.

Pa particles: The Pa particles are made up of a mixture of 75% Boswellia serrata extract and 25% sorbitol monostearate, and prepared according to a hot melt coating technique well known to the person skilled in the art, in order to prevent direct contact between the plant extract and the patient's oral mucosa. Therefore the Pa particles present very low solubility in saliva (inside the oral cavity): indeed a quantity less than 10% of the mass of the active ingredient (Boswellic acid) is dissolved after 10 seconds when the "reference test for determining particle solubility in saliva" defined above is applied, so as to prevent an unpleasant sensation. Granulometric analysis of the Pa particles according to the sieving method shows that more than 90% of them are less than 710 µm in size and less than 10% are less than 125 µm in size.

Ps particles: The Ps particles are made up of a mixture composed of 99% erythritol and 1% citric acid, and are obtained by granulation. The particles present an apparent density of around 0.8 g.cm$^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 µm in size and less than 10% are less than 125 µm in size.

Example 9

Preparation of One Kilogram (1 kg) of Food Supplement Based on Whitania Somnifera Composed of a Homogeneous Mixture of Pa and Ps Particles 40% by weight Pa particles and 60% by weight Ps particles are introduced into a rotary drum mixer, and are stirred for 15 minutes to form a homogenous mixture of particles.

Pa particles: The Pa particles are made up of a mixture of 75% Whitania somnifera extract and 25% sorbitol monostearate, and prepared according to a hot melt coating technique well known to the person skilled in the art, in order to prevent direct contact between the plant extract and the patient's oral mucosa. Therefore the Pa particles present very low solubility in saliva (inside the oral cavity): indeed a quantity less than 5% of the mass of the active ingredient (glycowithanolide) is dissolved after 10 seconds when the "reference test for determining particle solubility in saliva" defined above is applied. Granulometric analysis of the Pa particles according to the sieving method shows that more than 90% of them are less than 710 µm in size and less than 10% are less than 125 µm in size.

Ps particles: The Ps particles are made up of a mixture composed of 99% erythritol and 1% citric acid, and are obtained by granulation. The particles present an apparent density of around 0.8 g.cm$^{-3}$, and rapid solubilisation in saliva—in less than 20 seconds—when the "reference test for determining particle solubility in saliva" defined above is applied. Granulometric analysis of the Ps particles according to the sieving method shows that more than 90% of them are less than 710 µm in size and less than 10% are less than 125 µm in size.

Example 10

Preparation of One Kilogram (1 kq) of Pharmaceutical Preparation Based on Paracetamol Composed of a Homogeneous Mixture of Pa and Ps Particles 62.5% by weight Pa particles and 37.5% by weight Ps particles are introduced into a rotary drum mixer, and are stirred for 15 minutes to form a homogenous mixture of particles.

Pa particles: The Pa particles are made up of a mixture of 80% paracetamol and 20% sorbitol monostearate, and prepared according to a hot melt coating technique well known to the person skilled in the art, in order to prevent direct contact between the paracetamol and the patient's oral mucosa. Therefore the Pa particles present very low solubility in saliva (inside the oral cavity): indeed a quantity of less than 5% of the mass of active ingredient paracetamol is dissolved after 10 seconds when the "reference test for determining particle solubility in saliva" defined above is applied, so as to prevent a risk of absorption via the oral mucosa. Granulometric analysis of the Pa particles according to the sieving method shows that more than 90% of them are less than 500 µm in size and less than 10% are less than 125 µm in size.

Ps particles: The Ps particles are made up of a mixture composed of 90% erythritol, 9% tricalcium citrate and 1% citric acid, and are obtained by granulation. The particles present an apparent density of around 0.8 g.cm$^{-3}$, and rapid solubilisation in saliva according to the "reference test for determining particle solubility in saliva" defined above. Granulometric analysis of the Ps particles according to the sieving method shows that more than 90% of them are less than 710 µm in size and less than 10% are less than 125 µm in size.

Example 11

Evaluation of the Properties of the Composition According to the Invention in Terms of Rapidity of Ingestion and Ease of Swallowing A study encompassing 10 subjects aged between 12 and 77 years inclusive (of which 5 women and 5 men) was conducted in order to evaluate the properties of the invention in terms of rapidity of ingestion and ease of swallowing.

The rapidity of ingestion criterion was evaluated as follows:
A: Less than 10 seconds
B: Between 10 seconds and 20 seconds
C: Between 20 seconds and 30 seconds
D: More than 30 seconds The ease of swallowing criterion was evaluated as follows:
1: No difficulty in swallowing
2: Slight discomfort in swallowing
3: Medium discomfort in swallowing
4: Severe discomfort in swallowing The composition described in example 1 was evaluated and table 2 below brings together the results obtained.

TABLE 2

| Subject | Age | Sex | Ingestion time | Ease of swallowing |
|---|---|---|---|---|
| 1 | 24 | F | A (5 s) | 1 |
| 2 | 47 | M | A (4 s) | 1 |
| 3 | 35 | F | A (7 s) | 1 |
| 4 | 15 | M | A (4 s) | 1 |
| 5 | 68 | F | B (9 s) | 1 |
| 6 | 12 | F | A (8 s) | 1 |
| 7 | 77 | M | A (8 s) | 1 |
| 8 | 64 | M | A (5 s) | 1 |
| 9 | 33 | F | A (4 s) | 1 |
| 10 | 29 | M | A (4 s) | 1 |

Results Obtained:

Ingestion time: all the subjects were able to ingest the composition according to example 1 in less than 10 seconds (of which 5 subjects in less than 5 seconds).

Ease of swallowing: all the subjects swallowed the composition very easily and did not observe any discomfort upon swallowing.

The composition according to the invention makes it possible to obtain a galenic form or packaging in the form of a mixture of particles in sachet or stick form. Therefore the invention also relates to a dose of active ingredient in the form of the mixture described above, preferably bagged hermetically in an oblong or rectangular container, part of which can be easily torn off. Such presentations are also an object of the invention.

Advantageously, the total mass of the composition according to the invention that can be used for administering a dose of active ingredient(s) to a human being may range from 0.1 mg to 10 g, advantageously from 0.5 g to 5 g, and preferably from 1 g to 3 g.

The invention also relates to use of Ps particles such as described above for the manufacture of a composition in the form of a mixture of particles, in particular that described in the present application.

The invention also relates to the use of Pa particles such as described above for the manufacture of a composition in the form of a mixture of particles, in particular that described in the present application.

The invention also relates to a method of administering a dose of active ingredient(s) to a human or animal individual by ingestion of a mixture of particles as described in the present application. In particular, this method comprises placing the mixture of solid particles directly on the tongue. Advantageously, no additional/exogenous liquid ingestion (for example in the form of a glass of water) is required.

The invention also relates to a manufacturing method of the mixture described above.

This method comprises a step of mixing the Pa and Ps particles to obtain a homogeneous mixture of non-agglomerated solid particles. According to a preferred aspect, the Ps and Pa particles are manufactured prior to the mixing step.

The invention claimed is:

1. A solid composition for administration to a human or animal individual comprising:
   Pa particles comprising at least one active ingredient in sufficient quantity to administer a desired dose of active ingredient to said human or animal individual, wherein the Pa particles have very low solubility in saliva, and
   Ps particles comprising at least one polyol with low glycaemic index and at least one natural index and at least one natural organic acid or a salt thereof, the weight ratio of the at least one natural organic acid or salt thereof/the at least one polyol with low glycaemic index being between 0.01 and 1 inclusive, the Ps particles having an apparent density equal to or greater than approximately 0.6 g.cm$^{-3}$ and being rapidly soluble in saliva;
   wherein said Ps particles are present in said composition in sufficient quantity to enable rapid ingestion and facilitated swallowing of said Pa particles in said human or animal individual; and
   wherein the composition is in the form of non-agglomerated solid particles.

2. The composition according to claim 1, comprising a homogeneous mixture of Pa and Ps particles.

3. The composition according claims 1, wherein said at least one natural organic acid, or a salt thereof, is present in the Ps particles in a mass percentage not exceeding 50% of the total mass of the Ps particles.

4. The composition according to claim 1, wherein the Ps particles have an average size less than or equal to approximately 500 μm.

5. The composition according to claim 1, wherein the Ps particles are free from disintegrating agents.

6. The composition according to claim 1, wherein the Pa particles are made up of or are coated with a hydrophobic material,
   wherein the Pa particles are protected from moisture, have limited solubility in saliva, or both; or
   wherein the release of at least one active ingredient contained therein in one or more parts of the digestive tract is modulated; or
   wherein the Pa particles are protected from moisture, have limited solubility in saliva, or both and wherein the release of at least one active ingredient contained therein in one or more parts of the digestive tract is modulated.

7. The composition according to claim 1, wherein the Pa particles have an average size of less than approximately 500 μm.

8. The composition according to claim 1, wherein the average size of the Ps particles and the average size of the Pa particles are no more than 50% different from each other.

9. The composition according to claim 1, wherein the composition is free from disintegrating agents.

10. The composition according to claim 1, wherein the ratio between the mass of Pa particles and the mass of Ps particles is less than 10.

11. The composition according to claim 10, wherein said ratio is less than or equal to 1.

12. A medicine or a food supplement for human or animal use, comprising the composition according to claim 1.

13. A sachet or stick comprising the composition according to claim 1.

14. Particles comprising at least one polyol with low glyaecmic index and at least natural organic acid or salt thereof, the weight ratio of the at least one natural organic acid or a salt thereof/the at least one polyol with low glycaemic index being between 0.01 and 1 inclusive, the particles having an apparent density equal to or greater than approximately 0.6 $g.cm^{-3}$ and being rapidly soluble in saliva.

15. The composition of claim 1, wherein the polyol is erythritol, and wherein the erythritol has a mass percentage of at least 50% of the total mass of the Ps particles.

16. The composition of claim 1, wherein the Ps particles consist of at least one polyol with low glycaemic index.

17. The composition of claim 16, wherein the polyol is erythritol.

18. The composition of claim 10 wherein the ratio between the mass of Pa particles and the mass of Ps particles is less than or equal to 2.5.

\* \* \* \* \*